US008215303B2

(12) United States Patent
Townsend et al.

(10) Patent No.: US 8,215,303 B2
(45) Date of Patent: Jul. 10, 2012

(54) BREATHING APPARATUS

(75) Inventors: Paul Townsend, Newcastle upon Tyne (GB); David Hodson, Tyne & Wear (GB)

(73) Assignee: Draeger Safety UK Limited, Blyth, Northumberland (GB)

( * ) Notice: Subject to any disclaimer, the term of this patent is extended or adjusted under 35 U.S.C. 154(b) by 216 days.

(21) Appl. No.: 12/482,105

(22) Filed: Jun. 10, 2009

(65) Prior Publication Data

US 2010/0147306 A1 Jun. 17, 2010

Related U.S. Application Data

(63) Continuation of application No. 10/537,722, filed as application No. PCT/GB03/05346 on Dec. 9, 2003, now abandoned.

(60) Provisional application No. 60/432,454, filed on Dec. 11, 2002.

(51) Int. Cl.
*A61M 16/00* (2006.01)
*A62B 7/00* (2006.01)

(52) U.S. Cl. ......... 128/204.26; 128/200.29; 128/201.23; 128/201.28; 128/205.24

(58) Field of Classification Search ............ 128/200.24, 128/200.27, 200.29, 201.21, 201.23, 201.27, 128/201.26, 201.28, 201.29
See application file for complete search history.

(56) References Cited

U.S. PATENT DOCUMENTS

| | | | | |
|---|---|---|---|---|
| 3,028,859 A * | 4/1962 | Mitchell | 128/204.26 |
| 4,197,841 A * | 4/1980 | Brauer et al. | 128/202.13 |
| 4,356,820 A | 11/1982 | Trinkwalder, Jr. | |
| 4,819,626 A | 4/1989 | Himmens | |
| 6,394,091 B1 | 5/2002 | Giorgini | |
| 2005/0066966 A1* | 3/2005 | King | 128/201.23 |

FOREIGN PATENT DOCUMENTS

| | | |
|---|---|---|
| DE | 1 153 258 | 8/1963 |
| DE | 27 20 681 | 11/1978 |
| DE | 10159219 | 6/2003 |

OTHER PUBLICATIONS

International Search Report re PCT/GB 03/05346 mailed Jan. 4, 2004.

* cited by examiner

*Primary Examiner* — Clinton T Ostrup
(74) *Attorney, Agent, or Firm* — DLA Piper LLP (US)

(57) ABSTRACT

A face mask (10) mechanically coupled to a lung demand valve (LDV) (12). The face mask (10) comprises a main mask and an inner mask (15) which fits over the wearer's mouth and nose. The interior of the inner mask (15) is in fluidic communication with the interior of the main mask (10) by means of non-return valves (16). The interior of the main mask is in fluidic communication with an inlet port (18) which is mechanically and fluidically coupled to a supply port (20) of an LDV. The LDV (12) includes a diaphragm and a cover (44) which comprises three parts (44*a*, 44*b*) and (44*c*). Exhaled air is used to flush the space around the diaphragm. Thus, any toxic or undesirable gas in the vicinity of the diaphragm is pushed out to atmosphere by the exhaled air flowing past and around the diaphragm.

7 Claims, 5 Drawing Sheets

BREATHING APPARATUS

CROSS REFERENCE TO RELATED APPLICATIONS

This is a continuation of U.S. patent application Ser.No. 10/537,722 filed on Aug. 1, 2005, which is a 371 of PCT/GB03/05346 filed Dec. 9, 2003, which claims benefit of 60/432,454 filed Dec. 11, 2002.

FIELD OF THE INVENTION

The present invention relates to self-contained breathing apparatus (SCBA) and particularly to breathing apparatus utilising a face mask and a second stage regulator, or so-called lung-demand-valve (LDV).

In a SCBA set breathing gas (usually air) is stored at a first, "high" pressure in a pressurized cylinder. From the cylinder the gas is conveyed to the user for breathing via at least one stage of regulator, in which the gas is reduced in pressure. It is preferable to have two stages of regulator each of which reduces the pressure. In such a system the first reduction in pressure takes place, as the gas leaves the cylinder, in a first stage regulator. The gas is stored in the cylinder at a pressure of typically up to 200 to 300 bar and after the first stage of pressure reduction has a pressure in the order of 7.5 bar. The gas is then considered to be at "medium" pressure. The medium pressure gas is then conveyed to a second stage regulator, usually a lung demand valve conveniently mounted on a face mask of a user. Here the gas is reduced in pressure to a slightly super-atmospheric pressure, at which the gas is breathable.

The lung demand valve is actuated by the breathing of the wearer of the mask, such that as the wearer inhales a diaphragm is displaced causing a valving member to open allowing breathable gas into an expansion chamber, from which it may be drawn into the lungs of the user.

An example of such apparatus is illustrated in schematic sectional view in FIG. 1, in which a face mask 10 is mechanically coupled to a lung demand valve 12, which in turn is in fluidic communication with a cylinder of breathing gas 13 via a hose 14. The face mask 10 comprises an inner mask 15 which fits over the wearer's mouth and nose. The interior of the inner mask 15 is in fluidic communication with the interior of the main mask 10 by means of so-called "oranasal" non-return valves 16, mounted on either. side of the inner mask, and the interior of the main mask is in fluidic communication via vents (not shown) with an inlet port 18 of the mask. The mask inlet port 18 is mechanically fluidically coupled to a supply port 20 of the LDV. The LDV 12 itself includes a valving member, a valve seat (neither shown) and an expansion chamber 22. The valving member is biased in the "valve closed" position in which it bears against the valve seat. However, the valving member may be displaced from the valve seat to allow medium pressure compressed air into the chamber 22 by movement of an actuator arm 24 mounted pivotally on the LDV. The compressed air arrives at the LDV from a rubber hose coupled to the LDV at medium pressure (approximately 7.5 bar). A distal end 24A of the arm bears against the diaphragm member 26 comprising a flexible apron portion 26A and, in the centre, a relatively rigid disc portion 26B. The apron portion 26A is mounted around its periphery in a correspondingly shaped housing portion 28 of the LDV. Beneath it is a spring 30 which exerts a biasing force on the diaphragm to keep the actuator arm 24 normally in such a configuration that the valve is slightly open. On the same side of the diaphragm as the spring 30 the housing portion 28 is open to atmosphere, through a rubber dust cover 32 which is clipped over the housing 28 to keep dust or other ambient particulates from contacting the diaphragm 26.

In equilibrium, the spring 30 positions the diaphragm 26 and hence the actuator arm 24 so that the valve is partially open. Accordingly, breathable gas, at slightly super atmospheric pressure, flows into the chamber and hence to the mask inlet port 18 at a constant, limited rate, and the pressure inside the LDV keeps the spring and diaphragm in an equilibrium position. As soon as the wearer of the mask inhales, a reduction in the pressure inside the mask 15 occurs. This reduction is transmitted to the LDV chamber 22. The diaphragm is in fluidic communication with the atmosphere through holes 34 in the base of the LDV housing. When the air pressure in the chamber 22 falls below the equilibrium, super-atmospheric pressure, the spring 30 is able to push the diaphragm, causing it to rise, which in turn causes the actuator arm 24 to rise until they adopt the position shown in FIG. 1. The result of this is that the compressed air flows into the chamber 22 at a greater rate during inhalation. Once inhalation has ceased the pressure in chamber 22 builds again to resume the equilibrium state of slightly super-atmospheric pressing down on the diaphragm and countering the force of the spring 30. This causes the actuator arm to urge the valve towards an equilibrium position in which the flow of breathable gas into the chamber 22 is reduced again.

In this way the valve acts to supply breathable air to the lungs of the wearer but "on demand", whilst keeping a constant low level of supply to maintain a positive (i.e. super atmospheric) pressure in the mask at all times, even during non-inhalation phases, so as to resist the ingress of smoke and noxious gases into the mask around its sides.

FIG. 2 shows schematically the exhalation phase. In the LDV the pressure in chamber 22, i.e. of air for inhalation, and spring 30 maintains the diaphragm 26 and actuator arm 24 in an equilibrium position shown in FIG. 2. Meanwhile, exhaled air in the inner mask 15 builds in pressure and at a one-way exhalation valve 36 overcomes a biasing spring 38 to allow an exhale valving member 40 to be displaced from its seat 42. The exhaled air is simply vented to atmosphere to outlets 39. Once exhalation ceases, the pressure of exhaled air in the face mask falls and biasing spring 38 closes the exhalation valve 36. The cycle of inhalation and exhalation then continues.

For the LDV to function, the diaphragm must be exposed to the external atmosphere on one side. In atmospheres containing relatively high concentrations of toxins it is conceivable that the external face of the diaphragm might be subjected to a gradual build up of toxins. Since the apron of the diaphragm is a thin membrane, typically of rubber or silicone, concerns have been expressed that in exceptional cases if the diaphragm faces this exposure repeatedly or for long periods this could lead to toxins diffusing through the membrane.

SUMMARY OF THE INVENTION

Accordingly, a need exists for an LDV and/or LDV/mask combination in which the likelihood of such a build up of toxins on the external face of the diaphragm is minimised or eliminated.

According to one aspect of the invention there is provided a lung demand valve device for use with breathing apparatus, for delivering breathable gas from a pressurised supply to a user wearing a face mask, for inhalation. The device comprises a body in which is housed a valve member, for controlling the rate of delivery of the breathable gas, a movable diaphragm having a first face exposed to pressure within the body and a second face exposed to pressure outside the body.

The diaphragm is responsive to the differential in pressure between its first and second faces to control the valve member. A duct is provided and arranged to direct exhaled air towards the second face of the diaphragm.

The device may be detachably mountable on a mask of a breathing apparatus. Alternatively the device may be permanently attached to a mask of a breathing apparatus. In an alternative arrangement the device is integral with a mask of a breathing apparatus.

The duct portion may be arranged to abut an exhalation port of a mask. The duct may be arranged to direct exhaled air to a region surrounding the second face of the diaphragm, so as to flush ambient gases from that region.

Preferably the device comprises a cover member arranged to extend around the device for preventing the ingress of dirt into the housing, and wherein the duct comprises a portion of the cover. The cover may comprise a plurality of portions which portions are detachably fixed together.

Preferably the device comprises locating means arranged to co-operate with a mask to inhibit rotation of the device relative to a mask.

According to another aspect of the present invention there is provided a lung demand valve suitable for use in a self contained breathing apparatus, in which fluid for breathing is conveyed to a user on inhalation. The lung demand valve comprises a first fluid path, a second fluid path, a flexible diaphragm, separating the first and second fluid paths, and wherein the second fluid path is open to the atmosphere.

According to a still further aspect of the present invention there is provided a cover suitable for use on a lung demand valve for a self contained breathing apparatus, in which fluid for breathing is conveyed to a user on inhalation. The lung demand valve comprises a first fluid path, and a diaphragm, enclosing at least a part of the first fluid path. The cover provides the lung demand valve with a second fluid path, so that the first and second fluid paths are separated by the diaphragm, and the second fluid path is open to the atmosphere, and wherein exhaled fluid is directed along the second fluid path to the diaphragm.

According to a still further aspect of the present invention there is provided a self-contained breathing apparatus in which fluid for breathing is conveyed to a user on inhalation. The apparatus comprises a face mask, connected to a lung demand valve, and worn by the user, a high pressure cylinder containing the fluid for breathing, a hose for conveying fluid from the cylinder to the lung demand valve. The lung demand valve comprises a first fluid path for conveying fluid for inhalation to the face mask, a second fluid path for conveying exhaled fluid from the face mask to the atmosphere; and a flexible diaphragm, separating the first and second fluid paths, wherein exhaled air is directed to the diaphragm.

Preferably the second fluid path is provided by a removable cover positioned over the lung demand valve.

The cover may be made of chemically resistant material.

BRIEF DESCRIPTION OF THE DRAWINGS

A preferred embodiment of the present invention will now be described, by way of example only, with reference to the accompanying drawings in which.

DETAILED DESCRIPTION OF THE PREFERRED EMBODIMENT

Figure 1:
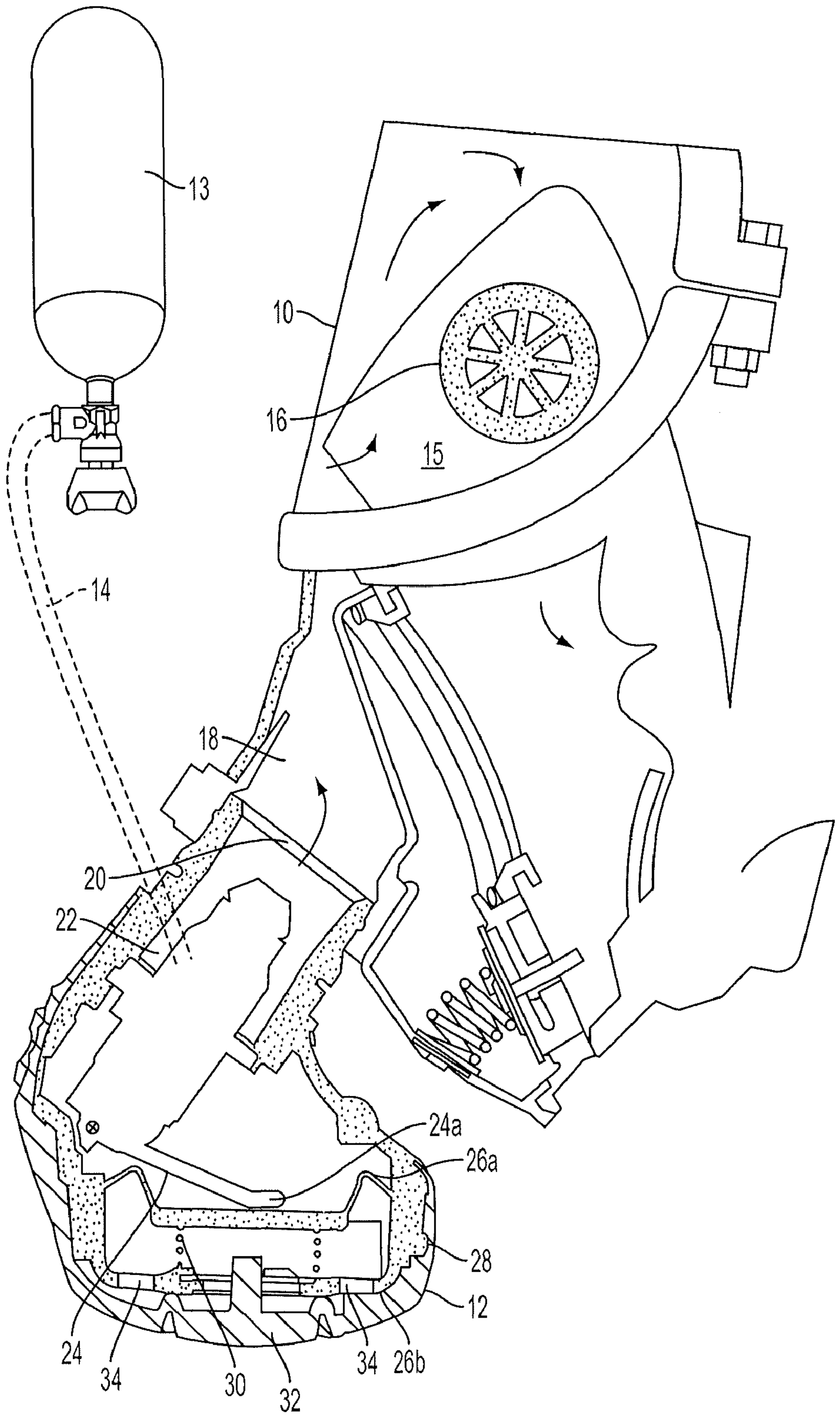
FIG. 1 PRIOR ART
FIG. 1 is a schematic sectional view of a prior known breathing mask and LDV in a first configuration.
Figure 2:
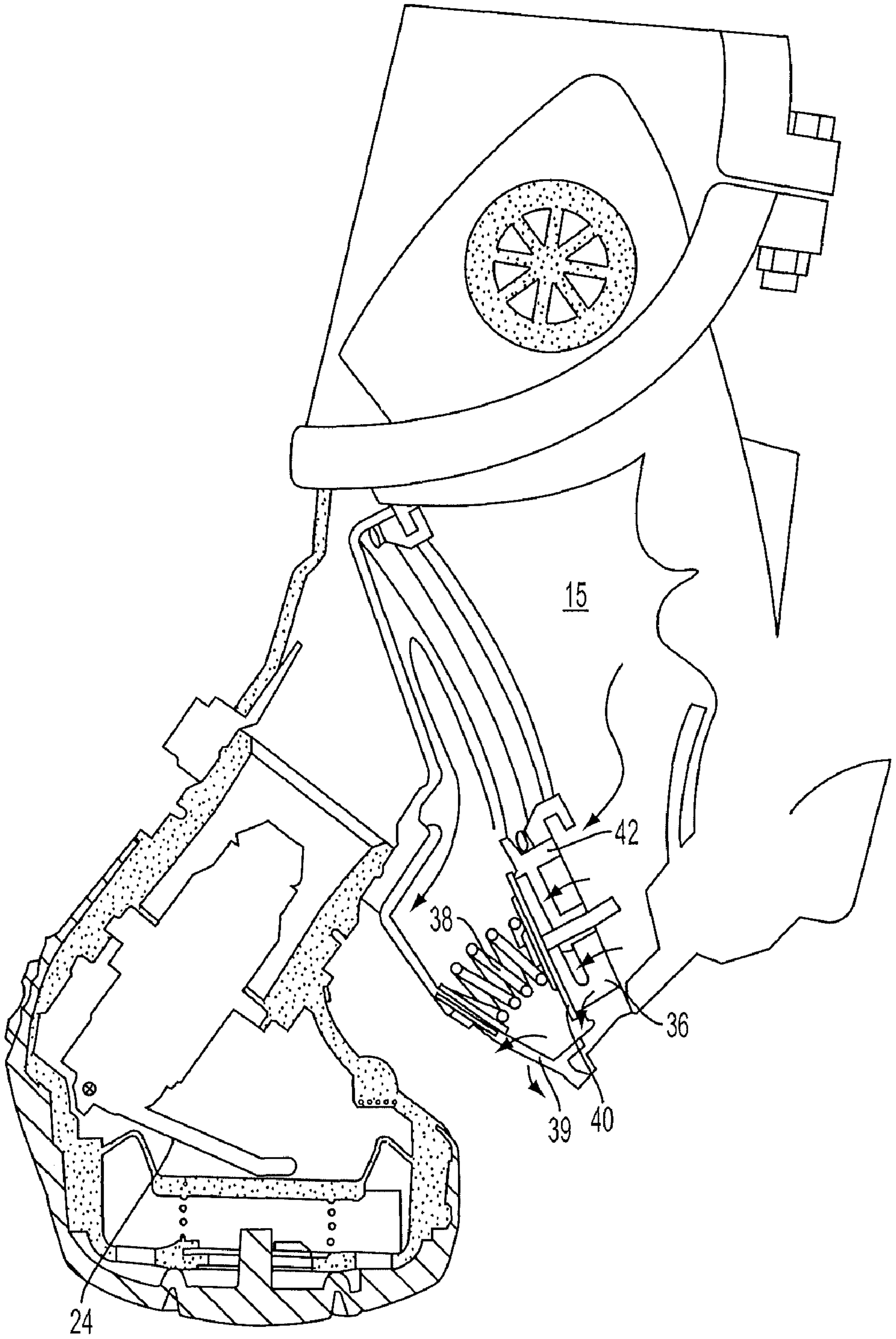
FIG. 2 PRIOR ART
FIG. 2 is a view of the mask of FIG. 1 in a second configuration.
Figure 3:
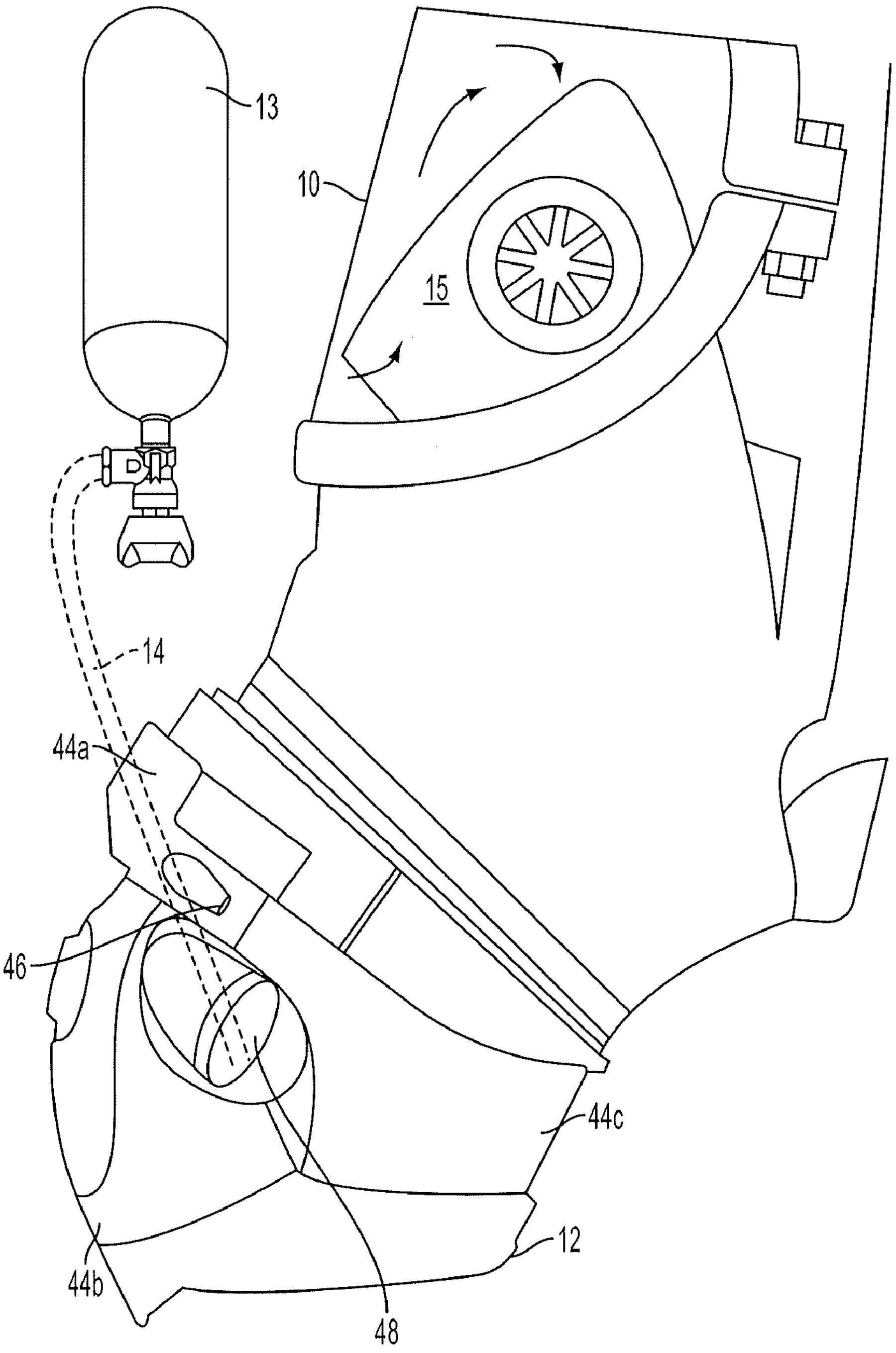
FIG. 3 is a side view of mask and LDV according to one exemplary embodiment of the invention.

Turning to FIG. 3, this is a side view of a mask and LDV constructed in accordance with one exemplary preferred embodiment of the present invention. In particular, FIG. 3 shows a mask 10, an LDV, generally represented by 12, a cylinder 13 and hose 14, and an inner mask 15 complete with non-return valve 16. The mask 10, LDV 12 cylinder 13 and hose 14 are identical to the equivalents, shown in FIGS. 1 and 2 and, during an inhalation phase, they operate in the same manner as the prior art apparatus described above.

However, in accordance with the present invention the LDV 12 is provided with a cover 44 which comprises three parts, namely, a yoke, 44*a*, a rubber cover portion 44*b* and a rigid plastic duct portion 44*c*.

The rigid plastic yoke 44*a* extends across the top of the supply port (not shown) of the LDV and is secured by screws 46 (only one of which is shown in FIG. 3). The screws are located on both sides of the yoke and threadedly engage the rigid plastic duct portion 44*c*. Stretched between the yoke 44*a* and the rigid plastic duct portion 44*c* across the front and underside of the LDV is the rubber cover portion 44*b*. In particular, the flexible rubber cover portion 44*b* is trapped between the yoke 44*a* and duct 44*c* at its upper end, and engages lugs (not shown) on the duct 44*c* at its lower end. A gap in the cover portion 44*b* reveals a compressed air intake port 48 which in the interest of clarity is shown in this figure unconnected to any delivery hose.

Figure 4:
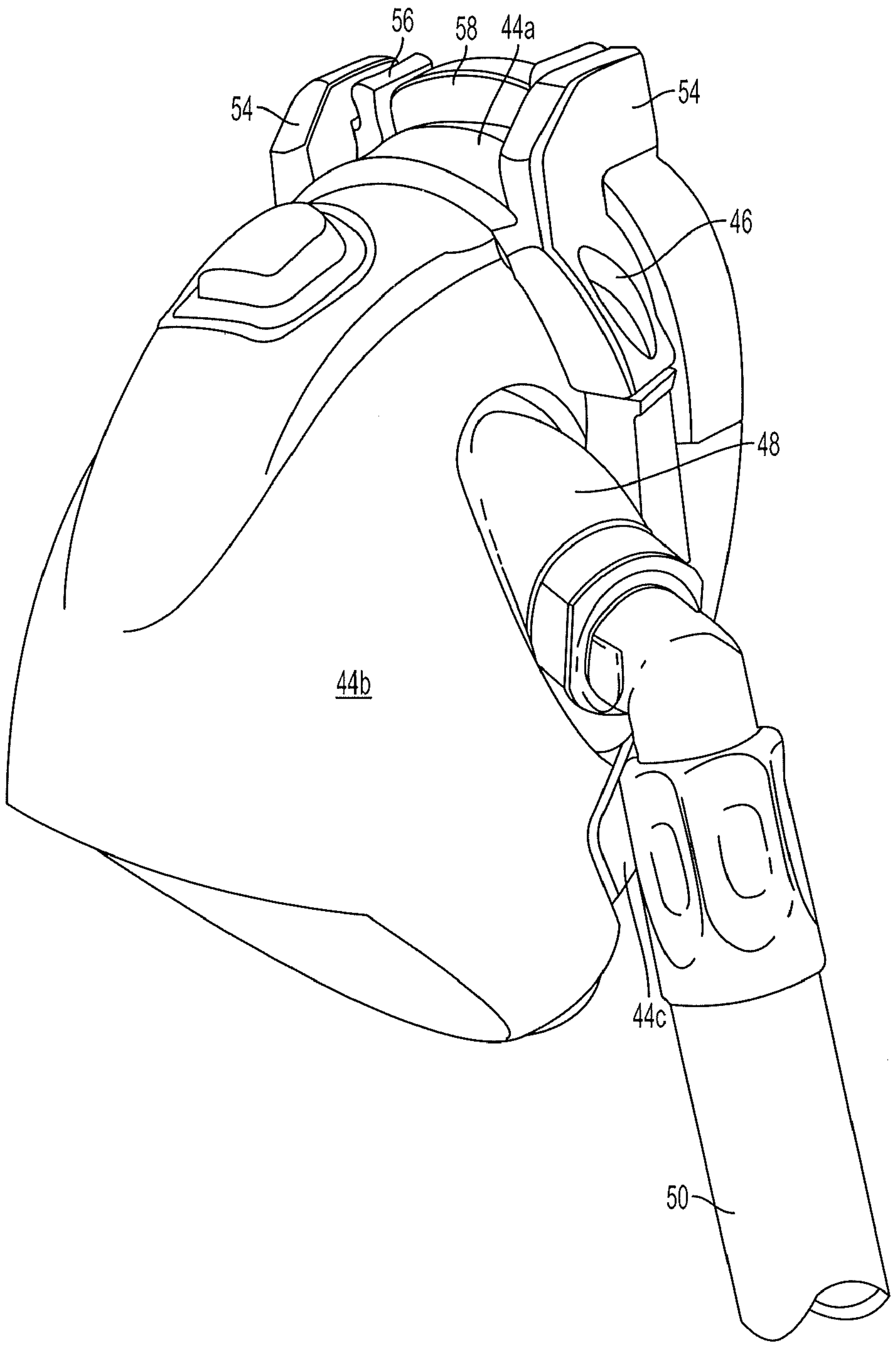
FIG. 4 is a front prospective view of the LDV of FIG. 3.

FIG. 4 shows generally the LDV 12 in a front perspective view. In FIG. 4, only parts 56, 58, and 60 of the face mask 10 to which the LDV is coupled are shown by hatched lines in the interest of clarity. A portion 50 of pressurised rubber hose is also shown connected to the intake port 48 of the LDV cover through which “medium” pressure air is supplied to the LDV.

Figure 5:
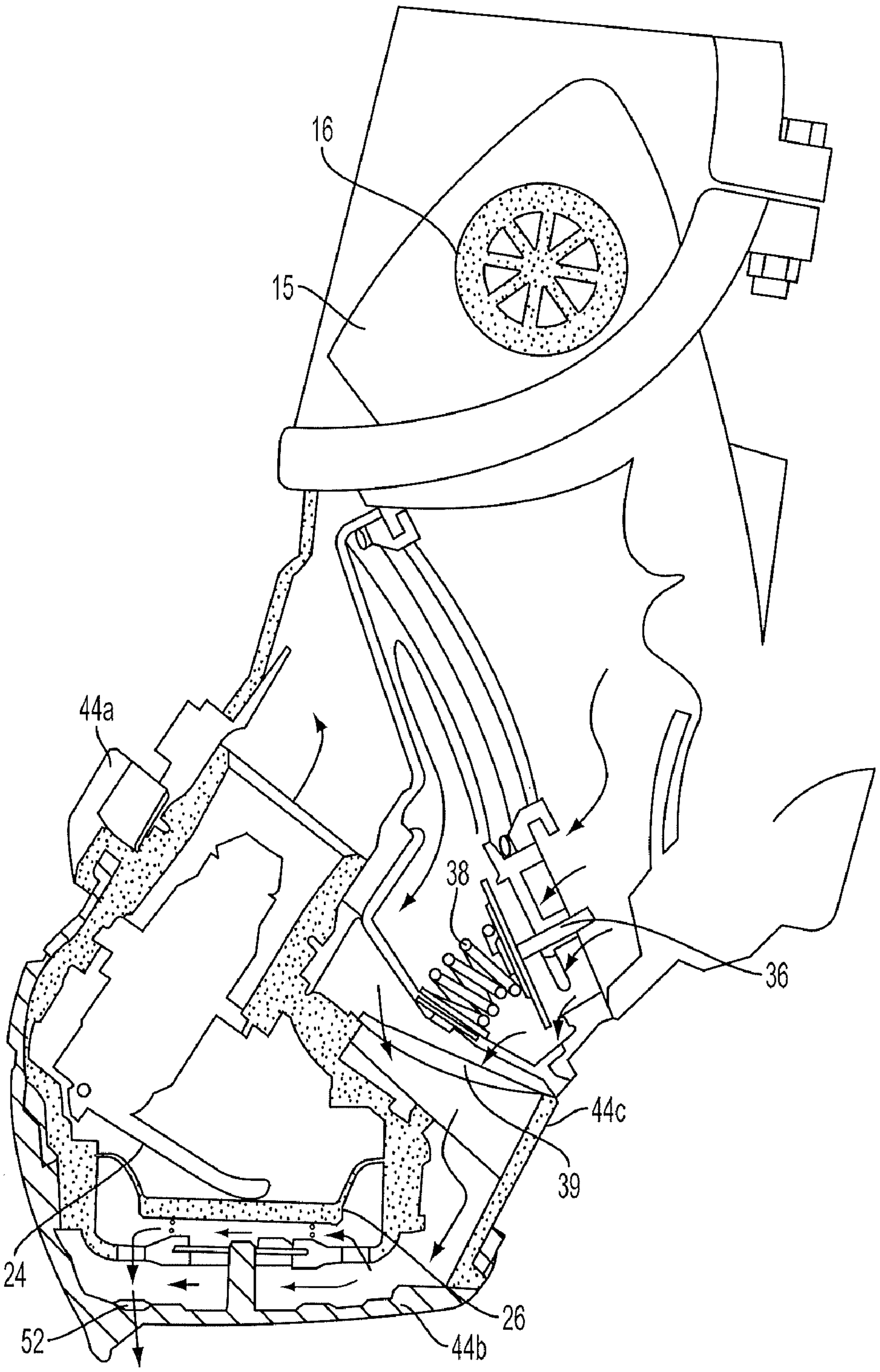
FIG. 5 is a schematic sectional view of the mask and LDV of FIGS. 3 and 4.

FIG. 5 shows a cross-sectional view of the mask. As the wearer exhales, an increased pressure is created in the inner mask 14. The increased pressure in the face mask lowers the diaphragm 26 in the LDV, temporarily closing the air supply. As the user breathes out, the exhalation valve 36 opens and allows the exhaled air to pass out of the mask 10 through outlet port 39. Since the duct portion 44*c* of the cover 44 abuts directly the port 39, exhaled air is retained within and directed by the cover 44. The air then flows over the diaphragm 26, and is eventually vented to the atmosphere through exit slots 52. When the user ceases exhaling, the exhalation valve 36 is urged shut by the spring 38, thus closing the exhalation port 39 to the atmosphere. The user then breathes in, and the process described above in relation to FIG. 1 is repeated.

Accordingly, exhaled air which in the prior art apparatus would be vented directly to the atmosphere is used to flush the space around the diaphragm. Thus, any toxic or undesirable gas in the vicinity of the diaphragm is pushed out to atmosphere by the exhaled air flowing past and around the diaphragm.

In the prior art LDV and mask the LDV is free to rotate in relation to the mask whilst remaining coupled thereto. Clearly in the apparatus according to the present invention the LDV must not be permitted to rotate with respect to the mask, since such rotation would displace the duct 44*c* from the exhalation port 39 and thus the exhaled air would undesirably vent directly to atmosphere before flushing the diaphragm 26.

To maintain the abutment of the duct 44*c* to the exhalation port 39, the yoke portion 44*a* of the cover is provided with two upstanding lugs 54 (see FIG. 4) which lie either side of a pair of similar lugs 56 on the face mask which are provided as standard items to protect a release button 58, located on the mask from being inadvertently depressed.

The juxtaposition of lugs 54 and 56 respectively on the yoke portion of the LDV cover and on the face mask, prevents rotation of the LDV, and hence the duct 44*c*, with respect to the mask.

While the invention has been described in detail and with reference to specific examples thereof, it will be apparent to one skilled in the art that various changes and modifications can be made therein without departing from the spirit and scope thereof.

What is claimed is:

1. A lung demand valve device for use with breathing apparatus, for delivering breathable gas from a pressurized supply to a user wearing a face mask, for inhalation, the device comprising:

a body in which is housed a valve member, for controlling the rate of delivery of the breathable gas, a housing within which is mounted a movable diaphragm having a first face exposed to pressure within the body and a second face exposed to pressure outside the body, the diaphragm being responsive to the differential in pressure between its first and second faces to control an actuation arm of the valve member, wherein the housing comprises a base having at least one hole therein which is positioned away from the second face of the diaphragm, and a duct arranged to direct exhaled air past and around said second face of said diaphragm through the at least one hole in the base, wherein the duct comprises:

a rigid duct portion attached to the housing and arranged to abut an outlet port of a face mask; and a flexible cover portion which extends between the housing and the rigid duct portion, and over the base, thereby preventing the ingress of dirt into the housing.

2. The device according to claim 1, wherein the device is arranged to be detachably attached to a face mask of a breathing apparatus.

3. The device according to claim 1 wherein the device is permanently attached to a mask of a breathing apparatus.

4. The device according to claim 1 wherein the device is integral with a mask of a breathing apparatus.

5. The device according to claim 1 wherein the duct is arranged to direct exhaled air to a region surrounding the second face of the diaphragm, so as to flush ambient gases from said region.

6. The device according to claim 1 wherein the device comprises locating means arranged to co-operate with a mask to inhibit rotation of the device relative to a mask.

7. A self-contained breathing apparatus including a lung demand valve device comprising:

a body in which is housed a valve member, for controlling the rate of delivery of the breathable gas, a housing within which is mounted a movable diaphragm having a first face exposed to pressure within the body and a second face exposed to pressure outside the body, the diaphragm being responsive to the differential in pressure between its first and second faces to control an actuation arm of the valve member, wherein the housing comprises a base having at least one hole therein which is positioned away from the second face of the diaphragm, and a duct arranged to direct exhaled air towards past and around said second face of said diaphragm through the at least one hole in the base, wherein the duct comprises:

a rigid duct portion attached to the housing and arranged to abut an outlet port of a face mask; and a flexible cover portion which extends between the housing and the rigid duct portion, and over the base, thereby preventing the ingress of dirt into the housing.

* * * * *